(12) United States Patent  
Takahashi et al.

(10) Patent No.: US 10,262,443 B2  
(45) Date of Patent: Apr. 16, 2019

(54) RADIATION IMAGING APPARATUS AND RADIATION IMAGE DETECTION METHOD

(71) Applicant: SHIMADZU CORPORATION, Kyoto (JP)

(72) Inventors: Wataru Takahashi, Kyoto (JP); Shinichiro Mori, Chiba (JP)

(73) Assignee: SHIMADZU CORPORATION, Kyoto (JP)

(*) Notice: Subject to any disclaimer, the term of this patent is extended or adjusted under 35 U.S.C. 154(b) by 0 days.

(21) Appl. No.: 16/021,102

(22) Filed: Jun. 28, 2018

(65) Prior Publication Data

US 2019/0012816 A1 Jan. 10, 2019

(30) Foreign Application Priority Data

Jul. 6, 2017 (JP) .................................. 2017-132993

(51) Int. Cl.
| | |
|---|---|
| G06T 5/00 | (2006.01) |
| G06T 11/00 | (2006.01) |
| G06T 3/40 | (2006.01) |
| H04N 5/32 | (2006.01) |
| H04N 5/365 | (2011.01) |

(52) U.S. Cl.
CPC .......... *G06T 11/008* (2013.01); *G06T 3/4053* (2013.01); *G06T 5/002* (2013.01); *H04N 5/3651* (2013.01); *G06T 2207/20182* (2013.01)

(58) Field of Classification Search
CPC ......... G06T 11/008; G06T 2204/20182; G06T 3/4053; G06T 5/002; H04N 5/3651
See application file for complete search history.

(56) References Cited

U.S. PATENT DOCUMENTS 9,754,389 B2 9/2017 Goshen  
2018/0108156 A1* 4/2018 Kobayashi ............ G06T 11/005

FOREIGN PATENT DOCUMENTS

JP 2015525648 9/2015

* cited by examiner

*Primary Examiner* — Mark R Gaworecki  
(74) *Attorney, Agent, or Firm* — Andrew F. Young, Esq.; Lackenbach Siegel, LLP

(57) ABSTRACT

A radiation imaging apparatus includes an irradiation element that irradiates a radiation, a radiation detection, an image generation element that generates a radiation image, a memory element that stores a principal component and a location detection element that detects and extracts a specific region from the radiation image by a matching using each contribution rate relative to each template image and each radiation image.

7 Claims, 8 Drawing Sheets

RADIATION IMAGING APPARATUS AND RADIATION IMAGE DETECTION METHOD

CROSS REFERENCE TO RELATED APPLICATIONS

This application relates to, and claims priority from JP 2017-132993 filed Jul. 6, 2017, the entire contents of which are incorporated herein by reference.

FIGURE SELECTED FOR PUBLICATION

FIG. 1

BACKGROUND OF THE INVENTION

Field of the Invention

The present invention relates to a radiation imaging apparatus and a detection method of a radiation image.

Description of the Related Art

Conventionally, a technology by which a specific region of a subject is detected by an image recognition from a radiation image of the subject, which is taken by a radiation apparatus is known.

For example, relative to the radiation therapy that treats the region to be medically treated, such as a tumor, with irradiation of an X-ray or a particle beam, the region to be treated (treatment region) moves depending on the body movement of the subject and the movement of an organ inside the body. Therefore, the irradiation of the radiation for the medical treatment using the radiation treatment apparatus is controlled in accordance with the detected location of the specific region by detecting the treatment region as the specific region by imaging the radiation image (radiograph) during the radiation therapy.

When the specific region is detected from the radiation image, a noise incorporated in the radiation image is a factor that impairs the accuracy level of detection. As a technology to reduce the noise, the Patent Document 1 discloses the steps of acquiring images at a variety of resolution levels from high-resolution to low-resolution, performing a principal component analysis relative to the images at the variety of resolution levels, and reconstructing the image in which the noise component is removed by replacing such image to the principal component image.

RELATED PRIOR ART DOCUMENTS

Patent Document

Patent Document 1: JP Patent Published 2015-525648 A

ASPECTS AND SUMMARY OF THE INVENTION

Objects to be Solved

However, the method according to the Patent Document 1, a number of images each having a different resolution are subject to the principal component analysis and then the image is reconstructed, so that it is difficult to reconstruct the image from which the noise is removed in real time during the medical treatment (treatment in short). Accordingly, even when the noise is included in the radiograph, it is preferable that the effect of the noise is suppressed, and the specific region is detected as quick as possible.

The present invention has been proposed in order to solve the aforementioned problems, and object of the present invention is to provide a radiation imaging apparatus and a detection method of the radiation image (radiograph) by which the specific region can be detected quickly while the effect of the noise is being suppressed even when the noise is included in the radiation image.

Means for Solving the Problem

To achieve the above purpose, a radiation imaging apparatus according to the first aspect of the present invention comprises: an irradiation element that irradiates a radiation to a subject; a radiation detection element that detects the radiation that transmits through the subject; an image generation element that generates an image based on a detection signal of the radiation detection element; a memory element that stores a principal component of a specific region obtained by a principal component analysis relative to a template image incorporating the specific region of the subject; and a location detection element that acquires a contribution rate of the principal component stored in the memory element relative to each template image and each radiation image generated by the image generation element, and detects a location of the specific region from the radiation image based on a matching using respectively obtained contribution rates.

According to the first aspect of the present invention, the radiation imaging apparatus, as set forth above, comprises the location detection element that acquires the template image and the contribution rate of the principal component stored in the memory element relative to each radiograph generated by the image generation element, and detects the location of the specific region from the radiograph based on the matching using each obtained contribution rate. Thereby, the detection of the specific region can be executed using the contribution rate to each template image and each radiograph of the principal component acquired from the template image. In such case, the principal component analysis is not performed on the radiation image that is newly generated by the image generation element and instead, the contribution rate relative to the radiation image is just acquired using the result of the principal component analysis relative to the template image prepared in advance, so that the detection processing can be achieved quickly. Then, the radiograph (including the noise) generated by the image generation element is not used as-is and instead, the principal component of the template image is used as a measure (scale) of the contribution rate, so that the matching can be performed while suppressing the effect of the noise included in the original radiograph. As a result, even when the noise is included in the radiation image, the specific region can be detected quickly while the effect of the noise is being suppressed.

The radiation imaging apparatus according to the first aspect, as set forth above, preferably, the location detection element detects the location of the specific region based on the difference between the average value of the contribution rates of the principal components relative to a plurality of templates and the contribution rate of the principal component relative to the radiation image. According to such constitution, the difference level of the radiation image from the common element (averaged image) to each template image, when the principal component is as a measure thereof, is obtained from the difference of the contribution rate between each template and each radiograph, so that the specific region can be detected accurately based on that the difference level is getting smaller. In addition, the specific region is detected by just performing the matching between contribution rates and it is different from the case in which the template matching is performed between the images.

The radiation imaging apparatus according to the first aspect, as set forth above, preferably, the location detection element performs matching using the first principal component to the Nth principal component (N is an integer between 2 and 100) that is stored in the memory. In such a constitution, just the number N principal components up to 100 principal components are used, so that the detection of the specific region can be executed quickly. In addition, the data needed to accurately detect the specific region while removing the noise component can be included in the principal components by the superordinate (in the front) Nth, so that the detection processing can be performed quickly with satisfactorily and required accuracy.

The radiation imaging apparatus according to the first aspect, as set forth above, preferably, the location detection element acquires the contribution rate using the principal component acquired from the template image incorporating no secondary particle beam that occurs along with the particle beam treatment, detects the specific region from each radiograph generated in series by the image generation element even during the particle beam treatment, and tracks the movement of the specific region. Here, the secondary particle beam is the particle beam that occurs secondarily inside the body of the subject due to the irradiation of the medical treatment particle beam to the treatment region and includes positron, neutron and prompt gamma ray and so forth. The secondary particle beam is incorporated in the radiation image as the noise during the particle beam treatment (while irradiation). Then, the contribution rate is acquired using the principal component acquired from the template image having no incorporated secondary particle beam, so that the effect of the secondary particle beam can be effectively canceled from the radiation image incorporating the secondary particle beam (noise). As a result, the effect of the secondary particle beam (noise) can be effectively suppressed.

According to the radiation imaging apparatus according to the first aspect, as set forth above, preferably, the template image is the partial image of the radiation image acquired in advance, which is extracted (cut out) and acquired therefrom so that the image includes the specific region, the location detection element acquires the contribution rate relative to the image portion in the detection window that is set up in the radiation image generated by the image generation element, and the matching is performed using the contribution rate by moving the detection window in series, by which the specific region is detected from the radiation image. In such constitution, for example, when the area of the radiation image, in which the specific region is included, is approximately understood, the search area is narrowed by the detection window, so that the matching is no longer required for the entire radiation image. As a result, the detection processing can be further performed quickly.

According to the radiation imaging apparatus according to the first aspect, as set forth above, preferably, the location detection element detects the location of the specific region by matching the principal component image of the template image generated from the contribution rate relative to the template image and the principal component and the conversion image that is the radiation image converted by the contribution rate relative to the radiation image and the principal component. In such constitution, the principal component image and the conversion image are reconstructed using the acquired contribution rate and the principal component, so that the matching between images can be performed. Even in such case, the principal component image that is converted by the principal component of the template image and the conversion image are used, so that the matching can be performed while the effect of the noise included in the original radiation image is being suppressed.

According to the radiation image detection method according to the second aspect, the radiation image detection method is a method that detects a specific region from a radiation image of a subject comprises a step of acquiring a principal component of the subject using a principal component analysis relative to a plurality of template images incorporating the specific region of the subject, a step of generating a radiation image by detecting the radiation that is irradiated to the subject and transmits through the subject, a step of acquiring a contribution rate of the principal component relative to each of the template image and the radiation image, and a step of detecting a location of the specific region from the radiation image by matching using each acquired contribution rate.

According to the second aspect of the present invention, the radiation image detection method, as set forth above, comprises the step of acquiring the contribution rate of the principal component relative to each of the template image and the radiation image, and the step of detecting the location of the specific region from the radiation image by matching using each acquired contribution rate Thereby, the detection of the specific region can be executed using the contribution rate to each template image and each radiation image of the principal component acquired from the template image. In such case, the principal component analysis is not performed on the radiation image that is newly generated by the image generation element and instead, the contribution rate relative to the radiation image is just acquired using the result of the principal component analysis relative to the template image prepared in advance, so that the detection processing can be achieved quickly. Then, the radiation image (including the noise) generated is not used as-is and instead, the principal component of the template image is used as a measure of the contribution rate, so that the matching can be performed while suppressing the effect of the noise included in the original radiation image. As a result, even when the noise is included in the radiation image, the specific region can be detected quickly while the effect of the noise is being suppressed.

Effect of the Invention

According to the aspect of the present invention, as set forth above, even when the noise is included in the radiation image, the specific region can be detected quickly while the effect of the noise is being suppressed.

The above and other aspects, features and advantages of the present invention will become apparent from the following description read in conjunction with the accompanying drawings, in which like reference numerals designate the same elements.

DETAILED DESCRIPTION OF THE PREFERRED EMBODIMENTS

Figure 1:
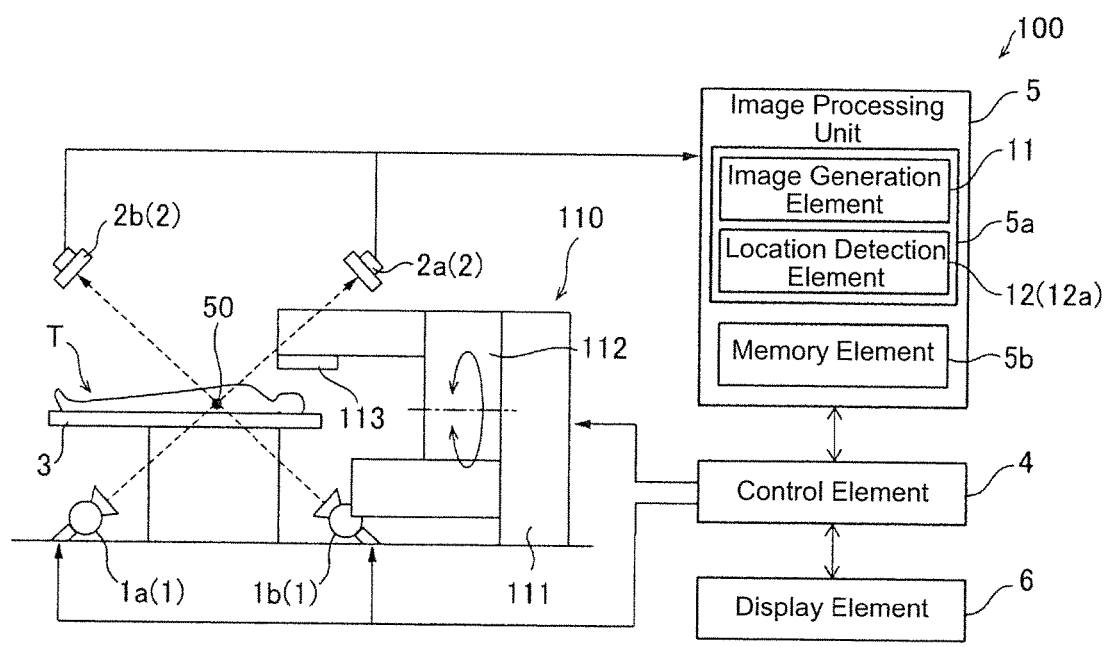
FIG. 1 is a schematic view illustrating an entire structure of a radiation imaging apparatus according to the aspect of the Embodiment 1.

Reference will now be made in detail to embodiments of the invention. Wherever possible, same or similar reference numerals are used in the drawings and the description to refer to the same or like parts or steps. The drawings are in simplified form and are not to precise scale. The word 'couple', 'link', 'connect', 'transfer' and similar terms do not necessarily denote direct and immediate connections, but also include connections through intermediate elements or devices. For purposes of convenience and clarity only, directional (up/down, etc.) or motional (forward/back, etc.) terms may be used with respect to the drawings. These and similar directional terms should not be construed to limit the scope in any manner. It will also be understood that other embodiments may be utilized without departing from the scope of the present invention, and that the detailed description is not to be taken in a limiting sense, and that elements may be differently positioned, or otherwise noted as in the appended claims without requirements of the written description being required thereto.

Various operations may be described as multiple discrete operations in turn, in a manner that may be helpful in understanding embodiments of the present invention; however, the order of description should not be construed to imply that these operations are order dependent.

The inventor sets forth specific Embodiments of the present invention based on the following FIGs.

[Embodiment 1]

[System of a Radiation Imaging Apparatus]

Figure 2:
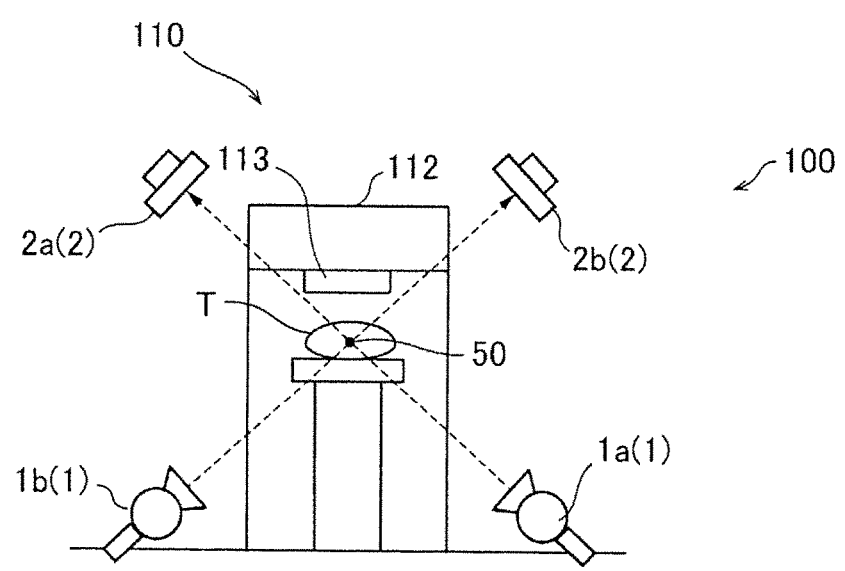
FIG. 2 is a schematic view illustrating the imaging directions of the X-ray image using the radiation imaging apparatus referring to FIG. 1.
Figure 3:
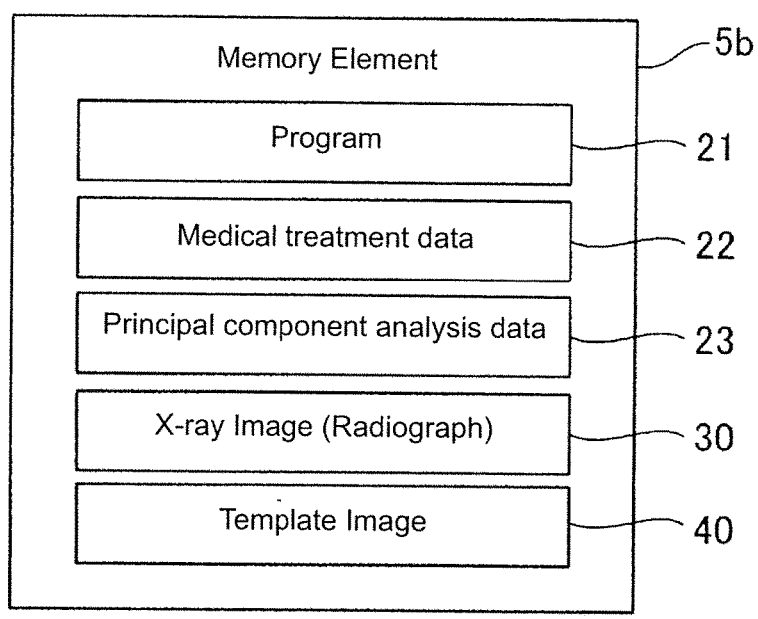
FIG. 3 is an explanatory diagram illustrating a memory element of the radiation imaging apparatus.

Referring to FIG. 1 to FIG. 3, the inventor illustrates the system of the radiation imaging apparatus 100 according to the aspect of the Embodiment 1 of the present invention.

Referring to FIG. 1, 2, the radiation imaging apparatus 100 is an apparatus that takes a radiation image that is imaging the inside of the subject T by irradiating a radiation from the outside of the subject T such as a human body and so forth. The radiation image (radiograph) is the image of the subject T, which is taken using the radiation that transmits the subject T. According to the aspect of the Embodiment 1, the radiation imaging apparatus 100 is an X-ray imaging apparatus that takes an X-ray image. Such X-ray image is one example of the radiation image.

According to the aspect of the Embodiment 1, the radiation imaging apparatus 100 constitutes a radiation medical treatment system that carries out the radiation (particle beam) therapy by being combined with the particle beam irradiation apparatus 110. The particle beam irradiation apparatus 110 is capable of irradiating the particle beam (treatment beam) to the subject T as a patient. The radiation imaging apparatus 100 detects the location of the specific region 50 from the X-ray image of the subject T. In such case, the specific region 50 is a tumor as the treatment target and a part of the body of the subject. The specific region 50 shifts along with body movement due to change of the posture and breathing of the subject T and so forth and physical activity such as heartbeat (pulsation) and with time. The radiation imaging apparatus 100 detects directly the location of the specific region 50 from the X-ray image using an image recognition under marker-less condition (without a maker member having a low X-ray transmittance) followed by performing dynamic tracking that tracks the shift of the specific region 50. The treatment beam is irradiated from the particle beam irradiation apparatus 110 to treat the specific region 50 (tumor) at the timing when the specific region 50 shifts to the irradiation location of the particle beam irradiation apparatus 110 while performing the dynamic tracking.

The particle beam irradiation apparatus 110 is capable of irradiating the particle beam including such as a proton beam and a heavy particle beam to the subject T on the table 3. The particle beam irradiation apparatus 110 comprises the examination table 111 (also known as couch), a gantry 112 that is swingable relative to the couch base (pedestal) 111 and a head 113 that is installed to gantry 112 and emits a therapeutic beam. Such particle beam irradiation apparatus 110 can change the irradiation direction of the therapeutic beam irradiated from the head 113 by swinging (oscillating) the gantry 112 relative to the couch base 111. Accordingly, such particle beam irradiation apparatus 110 can irradiate the therapeutic beam from a variety of directions to the specific region 50 such as a tumor and so forth of the subject T.

The radiation imaging apparatus 100 comprises an irradiation element 1 that irradiates a radiation (X-ray) to the subject T and an X-ray detection element 2 that detects the radiation (X-ray) that transmits the subject T. The irradiation element 1 and the X-ray detection element 2 are in-place facing each other, as a pair, sandwiching a table (examination table) 3 on which the subject T is loaded. The radiation imaging apparatus 100 further comprises a control element 4 that controls the irradiation element 1 and the table 3. The X-ray detection element 2 is an example of a "radiation detection element" in claim.

A plurality of pairs of the irradiation element 1 and the X-ray detection element 2 is installed. According to the aspect of the Embodiment 1, two pairs, the pair of the irradiation element 1a and the X-ray detection element 2a and the pair of the irradiation element 1b and the X-ray detection element 2b are installed. Each pair constitutes the first imaging system and the second imaging system that image the subject T from the different directions from each other. The 3-dimensional location of the specific region 50 (tumor) is identified based on the X-ray images generated from each imaging system. For example, the table 3 is shiftable relative to the orthogonal three axes (X-axis, Y-axis, Z-axis) and rotatable around each axis, i.e., shiftable in six axis-directions. In addition, the pair of the irradiation element 1 and the X-ray detection element 2 is horizontally shiftable in a periphery of the table 3.

The irradiation element 1 comprises an X-ray tube that emits an X-ray when high-voltages are added thereto. The irradiation element 1 is connected to the control element 4. The control element 4 controls the irradiation element 1 in accordance with the preset imaging conditions including the tube voltage, the electric current and the time-interval between X-ray irradiations and so forth and emits the X-ray from the irradiation element 1.

The X-ray detection element 2 that detects the X-ray, which the irradiation element 1 irradiates, that transmits the subject T, and outputs a detection signal corresponding to the detected X-ray strength. The X-ray detection element 2 comprises e.g., a FPD (flat panel detector). In addition, the radiation imaging apparatus 100 further comprises an image processing unit 5 that receives the X-ray detection signal from the X-ray detection element 2 and generates an X-ray image 30 (refer to FIG. 4). The X-ray detection element 2 outputs the X-ray signal having a predetermined resolution to the image processing unit 5.

The control element 4 is a computer comprising a CPU (central processing unit), ROM (read only memory) and RAM (random access memory) and so forth. The CPU executes the predetermined control program, so that the control element 4 is operative to control each unit of the radiation imaging apparatus 100. The control element 4 controls the irradiation element 1, the image processing unit 5, and the shift of the table 3. The radiation imaging apparatus 100 further comprises a display 6. The display 6 is a monitor such as e.g., a liquid crystal display and so forth. The control element 4 controls the display 6 to display the image that the image processing unit 5 generates. In addition, the control element 4 outputs the trigger signal to the particle beam irradiation apparatus 110 when the specific region 50, which is detected by the image processing unit 5, reaches to the irradiation location of the particle beam irradiation apparatus 110. Accordingly, the irradiation of the therapy (treatment) beam to the specific region 50 is performed highly accurately.

The image processing unit 5 is a computer comprising a processor 5a such as e.g., the CPU or a GPU (graphic processing unit), and the memory element 5b such as e.g., ROM and RAM. Specifically, the image processing unit 5 executes the image processing program 21 (referring to FIG. 3) stored in the memory element 5b by the processor 5a. The image processing unit 5 can be made with the control element 4 in a unified manner by executing the image processing program with the same hardware (CPU) as the control element 4.

The image processing unit 5 comprises the image generation element 11 and the location detection element 12 that are operative for the processor 5a to execute the image processing program 21. Each of the image generation element 11 and the location detection element 12 may comprises an individual and dedicated processor.

The image generation element 11 generates the X-ray images 30 (referring to FIG. 4) based on the detection signal that the X-ray detection element 2 detects. According to the aspect of the Embodiment 1, the X-ray images 30 is fluoroscopic images generated in a video format. Specifically, the irradiation element 1 intermittently irradiates the X-rays toward the subject T in a predetermined time-interval, and the X-ray detection element 2 detects such X-rays, in series, that transmit the subject T. The image generation element 11 converts the detection signals to images, which the X-ray detection element 2 outputs in series, to generate the X-ray images 30 by the predetermined frame rate. Such frame rate is e.g., approximately in the range of 15 FPS to 30 FPS. The image generation element 11 outputs the generated X-ray images 30 to the control element 4. The control element 4 displays the X-ray images 30 on the display 6.

The location detection element 12 detects the location of the specific region 50 from the X-ray images 30 generated by the image generation element 11. The location detection element 12 detects the specific region 50 using the image recognition. The location data relative to the specific region 50 are output to the control element 4.

Referring to FIG. 3, the memory element 5b stores the program 21 (imaging processing program) that functions the computer as the image processing unit 5. The memory element 5b stores the X-ray image 30 generated by the image generation element 11.

The memory element 5b stores a plurality of template images 40 incorporating the specific region 50 of the subject T and the treatment plan data 22. The template image 40 and the treatment plan data 22 are generated in advance prior to the particle beam treatment. The treatment plan data 22 includes four-dimensional CT (Computed Tomography) data generated by performing three-dimensional CT imaging continuously with time using the CT imaging. The treatment plan data 22 provides understandably the location, size, shape, shifting range and so forth of the specific region 50 relative to the subject T. The template image 40 is acquired by imaging the specific region 50 of the subject T using the radiation imaging apparatus 100 in accordance with the treatment plan generated based on the treatment plan data 22. The template image 40 is the partial image of the X-ray images 30 acquired in advance, which is cut out (extracted) and acquired and transferred therefrom so that the image includes the specific region 50. A plurality of template images 40 is generated in advance and stored in the memory element 5b.

In addition, according to the aspect of the Embodiment 1, the memory element that stores the principal component of the specific region 50 acquired from the principal component analysis relative to a plurality of template images 40 incorporating the specific region 50 of the subject T. Specifically, the memory element 5b stores the principal component analysis data 23 including the principal component of the specific region 50. The inventor sets forth the detail of the content of the principal component analysis data 23 later.

(Detection Processing of the Specific Region)

Figure 4:
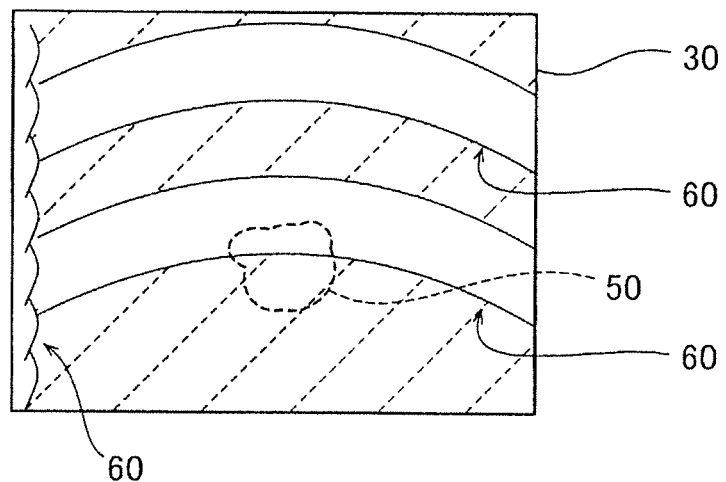
FIG. 4 is a schematic diagram illustrating the X-ray image.
Figure 5:
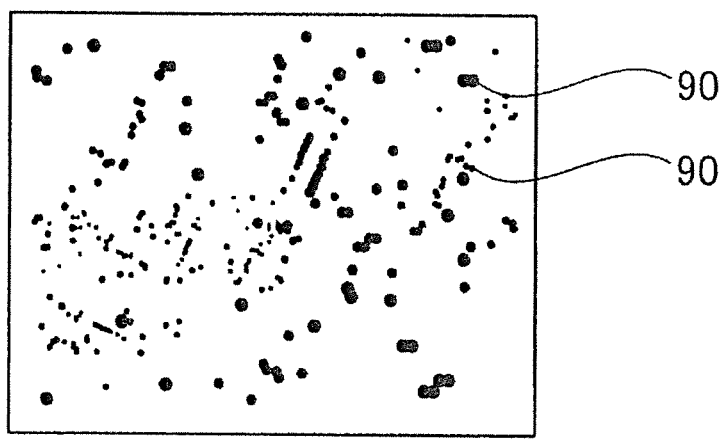
FIG. 5 is a schematic diagram illustrating the noise due to incorporation of the secondary particle beam.
Figure 6:
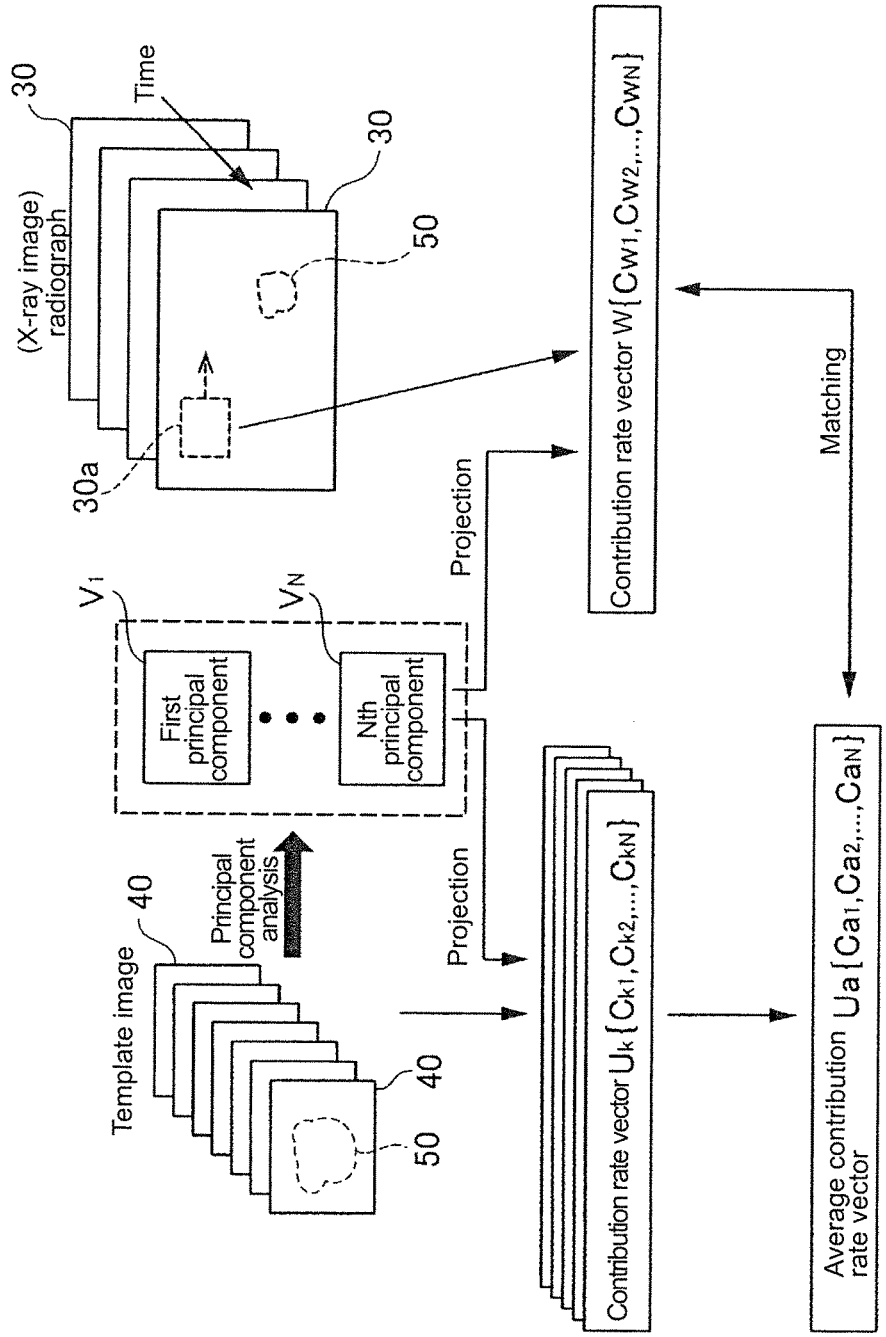
FIG. 6 is a schematic view illustrating a matching processing with the location detection element according to the aspect of the Embodiment 1.

Next, referring to FIG. 4-FIG. 6, the inventor sets forth the detection processing with the image processing unit relative to the specific region.

During the treatment, the relative locational relationship between the irradiation element 1, the X-ray detection element 2 and the table 3 is adjusted so that the specific region 50 of the subject T can be incorporated into the X-ray images 30. Referring to FIG. 4, the specific region 50 is overlapped with the structural portion 60 such as bone of the subject T or the other organs (not shown in FIG.) in the X-ray images 30 generated by the image generation element 11. When the specific region 50 is a tumor, the specific region 50 is not easily discriminated from others due to low visibility (contrast between the surrounding areas) thereof. In addition, when the therapeutic beam is irradiated, the secondary particle beam that takes place at the subject T is incorporated in the X-ray image 30. Referring to FIG. 4, the incorporated secondary particle beam is drawn as the hatching. Here, the secondary particle beam is the particle beam that occurs secondarily due to the irradiation of the therapeutic beam (particle beam) to the treatment region and includes positron, neutron and prompt gamma ray and so forth.

FIG. 5 is an image (schematic diagram) illustrating relative to the incorporation of the secondary particle beam into the X-ray image 30. The secondary particle beam is incorporated at the random location of the X-ray image 30 as a bright point 90 that is a point as an impulse-like noise. In addition, the size, the shape and intensity (pixel value) of the bright point 90 of the secondary particle beam varies in a variety of ways depending on the range of the secondary particle beam and the incident angle into the X-ray detection element 2 thereof. Specifically, the intensity distribution and the shape and so forth of the bright point 90 of the secondary particle beam are highly heterogeneous, so that it is characterized by that a general noise removal method such as filtering processing can be hardly applied thereto. When the bright point 90 of the secondary particle beam is overlapped with the specific region 50 and incorporated, the detection accuracy of the specific region 50 is worsened in addition to the low visibility of the specific region 50, so that the tracking for the specific region 50 is disturbed.

Therefore, according to the aspect of the Embodiment 1, the principal component analysis relative to a plurality of template images 40 incorporating the specific region 50 of the subject T is executed and then the memory element 5$b$ (referring to FIG. 3) stores the acquired data of the principal component of the specific region 50. And referring to FIG. 6, the location detection element 12 acquires each contribution rate $c_j$ of the template image 40 and the principal component $V_j$ stored in the memory element 5$b$ relative to each X-ray image 30 generated by the image generation element 11 and detects the location of the specific region 50 from the X-ray images 30 based on a matching using each obtained contribution rate Cj.

Here, the template images 40 and the X-ray images 30 are deemed as vectors in which the pixel value is the component. When the template image 40 is an image having (m×n) pixels, the template image 40 has the number (m×n) of the component and expressed as a vector having the pixel value (e.g., 0-255) of the pixel corresponding to each component. Given the number of the template images 40 is k, the template images 40 are the vectors $X_1$-$X_k$.

The principal component is obtained by solving the eigenvalue problem of the covariance matrix C represented by the following formula (1) relative to the vectors $X_1$-$X_k$.

[Mathematical formula 1]

$$C = \frac{1}{k}\sum_{i=1}^{k}\sum_{j=1}^{k}(\vec{\mu}-\vec{X}_i)(\vec{\mu}-\vec{X}_j)^T \quad (1)$$

Here, the vector μ is a vector of the average image of the template images 40 of the number of k.

Given the eigenvalue of the covariance matrix C is $\lambda_j$ and the eigenvector $V_j$, the eigenvector $V_j$ is the principal component and the absolute value of the corresponding eigenvalue λj is the coefficient representing the contribution rate of the principal component. The subscript $j$ is given based on the absolute value of the eigenvalue λ in order from the large to the small. At this time, the eigenvector $V_1$ is the first principal component, the eigenvector $V_2$ is the second principal component, and the eigenvector $V_N$ is the Nth principal component.

When the principal component analysis is executed in such way, the vector X of each template image 40 is expressed as the following mathematical formula (2) which expresses the linear sum of each principal component Vj that is orthogonal each other. The total number of the principal components coincides with the number (m×n) of the pixel of the template images 40.

[Mathematical formula 2]

$$\vec{X} = \vec{\mu} + c_1\vec{V}_1 + c_2\vec{V}_2 + \ldots + c_j\vec{V}_j \quad (2)$$

In the mathematical formula (2), the average image vector μ denotes the element common to each template image 40 and each principal component $V_j$ denotes an element corresponding to the individual difference of each template image 40. Here, the coefficient $c_j$ relative to each principal component $V_j$ denotes the contribution rate of each principal component $V_j$ relative to each template image 40. Specifically, the contribution rate cj corresponds to the size of the projection vector for which the vector X of each template image 40 is projected to each principal component $V_j$ and coincides with the scalar product of the vector X of each template image 40 and each principal component $V_j$. Specifically, the coefficient (contribution rate cj) relative to each principal component $V_j$ is the scalar product of the image (X-μ) obtained by subtracting the average image μ from each template image X and each principal component V (however, the size of the principal component is standardized (unit vectorized) to provide 1). The specific region 50 is commonly incorporated in the respective template images 40, so that each principal component $V_j$ reflects the individual difference (feature) of the specific regions 50.

Now, the featured point reflecting the individual difference of the specific regions 50 includes the shape and size of the specific region 50. Therefore, each superordinate principal component $V_j$ includes the data relative to the shape and size of the specific region 50. On the other hand, the noises, such as the secondary particle beam, incorporated regardless of the specific region 50 are the data included particularly in the subordinate principal component among the respective principal components $V_j$.

Accordingly, when executing the matching and considering the superordinate Nth principal components $V_N$ among the calculated principal components $V_j$, the specific region 50 can be detected only considering the effective element on discrimination of the specific region 50 while excluding the subordinate noise component to the Nth principal component.

According to the aspect of the Embodiment 1, the location detection element 12 performs matching using the components from the first principal component $V_1$ to the Nth principal component $V_N$ (N is an integer between 2 and 100) that are stored in the memory element 5$b$. It is preferable that a certain number of principal components are considered, e.g., preferably N is at least 10, to ensure the detection accuracy. When executing the matching and excluding the noise element, it is preferable that the number of principal components should not be too large and e.g., N is at most 80. According to the aspect of the Embodiment 1, for example, N is 30. Both excluding the noise element and ensuring the detection accuracy of the specific region 50 can be achieved considering by the 30th principal component V30.

According to the aspect of the Embodiment 1, the location detection element 12 acquires the contribution rate cj of the principal component Vj relative to a plurality of template images 40. For example, the location detection element 12 acquires respectively the contribution rate $c_j$ of the number N principal component $V_j$ relative to each template image 40 using the superordinate number N principal components $V_j$ from the first principal component to the Nth principal component.

For example, the location detection element 12 makes out the projection matrix Q to project the input image based on each principal component $V_j$ using the superordinate number N of the principal components $V_j$. The following mathematical formula (3) expresses the projection matrix Q. The N-dimensional contribution rate vector from the first principal component of the input image to the number N principal component thereof can be obtained by multiplying the vector of the input image (the template image 40 or a newly acquired X-ray image 30) by the projection matrix Q.

[Mathematical formula 3]

$$Q=\{\vec{V}_1,\ldots,\vec{V}_N\} \qquad (3)$$

The location detection element 12 makes out the N-dimensional contribution rate $U_k=\{c_{k1},\ldots c_{kN}\}$ (k=1~k) in which the contribution rates cj of each principal component Vj relative to each template image 40 are side-by-side by multiplying each template 40 by the projection matrix Q. According to the aspect of the Embodiment 1, the location detection element 12 makes out the average contribution rate vector $U_a=\{c_{a1},\ldots c_{aN}\}$ by averaging the contribution rate vectors $U_k$ of each made-out template image 40. Specifically, the location detection element 12 calculates the average value $c_{aj}$ (average contribution rate vector $U_a$) of the contribution rates $c_j$ of each principal component $V_j$ relative to a plurality (number k) of template images 40 and stores the results therefrom in the memory element 5b.

On the other hand, when detecting the specific region 50, the location detection element 12 acquires the contribution rate j of the principal component $V_j$ relative to the X-ray image 30 with respect to the X-ray image generated by the image generation element 11. For example, the location detection element 12 makes out the N-dimensional contribution rate vector $W=\{c_{w1},\ldots,c_{wN}\}$, in which the contribution rates $c_{wj}$ of each principal component $V_j$ relative to each X-ray image 30 are side-by-side, by multiplying each X-ray image 30 by the projection matrix Q.

The location detection element 12 detects the location of the specific region 50 based on the difference between the average value $c_{aj}$ of the contribution rates $c_j$ of the principal components $V_j$ relative to a plurality (number k) of template images 40 and the contribution rate cwj of the principal component $V_j$ relative to the X-ray images 30. Specifically, the location detection element 12 executes the matching based on the difference between the contribution rates that are the N-dimensional average contribution rate vector $U_a$ obtained by averaging the contribution rate vectors Uk of each template image, and the contribution rate vector W obtained by multiplying the X-ray image 30 by the projection matrix Q. For example, the location detection element 12 obtains a square error $D^2$ between the average contribution rate vector $U_a$ of each template image 40 and the contribution rate vector W of the X-ray image 30 by following mathematical formula (4).

[Mathematical formula 4]

$$D^2=\|\vec{U}_a-\vec{W}\|^2 \qquad (4)$$

Here, $U_a$ is an average contribution rate vector of the template images 40 and W is a contribution rate vector of the X-ray image 30.

According to the above mathematical formula (2), the template image 40 and the X-ray image 30 are approximated by the linear sum of each projection vector ($c_j$, $V_j$), so that the square error $D^2$ between the contribution rates denotes the degree of the difference between the average image of each template image 40 and the X-ray image 30 based on each principal component by the Nth principal component as a measure, and denotes that the smaller the square error $D^2$ is, the more the X-ray image 30 coincides with the template image 40 (i.e., the specific region 50 is present). Such square error $D^2$ is applied to the measure (score) of the similarity between the X-ray image 30 and the template image 40 relative to the matching. The value corresponding to the inverse of the square error $D^2$ can be applied as the measure (score) of the similarity upon the matching. In such case, the value of the score denotes the similarity instead of the degree of the difference.

In such way, the location detection element 12 detects the specific region 50 from the X-ray image 30. According to the aspect of the Embodiment 1, the principal component analysis data 23 that the memory element 5b stores includes each principal component $V_j$ acquired by the principal component analysis, the projection matrix Q, each contribution rate $c_j$ and the average contribution rate vector $U_a$.

In addition, according to the aspect of the Embodiment 1, the location detection element 12 acquires the contribution rate using the principal component acquired from the template image 40 incorporating no secondary particle beam that occurs along with the particle beam treatment, detects the specific region 50 from each X-ray image 30 generated in series by the image generation element 11 during the particle beam treatment, and tracks the shift of the specific region 50.

Specifically, the template image 40 is made out without incorporating the secondary particle beam by being acquired in advance under the state (before the treatment) in which the therapeutic beam is not irradiated. Therefore, the effect of the noise due to the secondary particle beam relative to each principal component $V_j$ obtained by the principal component analysis and the contribution rate $c_j$ is absolutely excluded and each principal component $V_j$ and the contribution rate $c_j$ reflects more the features of the specific region 50.

In addition, the location detection element 12 acquires the contribution rate $c_{wj}$ relative to the image portion in the detection window 30a that is set up in the X-ray image 30 generated by the image generation element 11, and performs the matching using the contribution rate $c_{wj}$ by shifting the detection window in series, by which the specific region 50 is detected from the X-ray image 30. Specifically, referring to FIG. 6, the location detection element 12 sets up the detection window 30a having the predetermined size in the X-ray image 30 acquired during the particle beam treatment and calculates the square error $D^2$ between the contribution rate vector W of the image portion within the detection window 30a and the average contribution rate vector $U_a$ of each template image 40. The location detection element 12 shifts the detection window 30a and calculates the square error $D^2$ in series. At this time, the estimate shifting range of the specific region 50 is known in advance based on the treatment plan data 22, so that the shifting range of the detection window 30a is limited to the part of the X-ray image 30. The shifting range of the detection window 30a is set up as the range to which the predetermined margin is added, e.g., the estimate shifting range of the specific region 50.

The location detection element 12 outputs, e.g., the location having the minimum value among the square errors D2 calculated within the shifting range of the detection window 30a as the detected location of the specific region 50. The detected location of the specific region 50 is output to the control element 4. The location detection element 12 executes a matching processing relative to the respective X-ray images 30 generated according to the predetermined frame rate during particle beam treatment. The control element 4 superimposes the identification, which denotes the detected location of the specific region 50, to the acquired X-ray image 30 and display such image on the display element 6. Referring to FIG. 4, the identification is e.g., the line indicating the profile of the specific region 50. The control element 4 updates the display element 6 and displays the X-ray image 30 and the detection location in the real-time video format every time when the new X-ray image 30 and the new detected location are obtained from the image processing unit 5.

(Processing Operation of the Radiation Imaging Apparatus)

Figure 7:
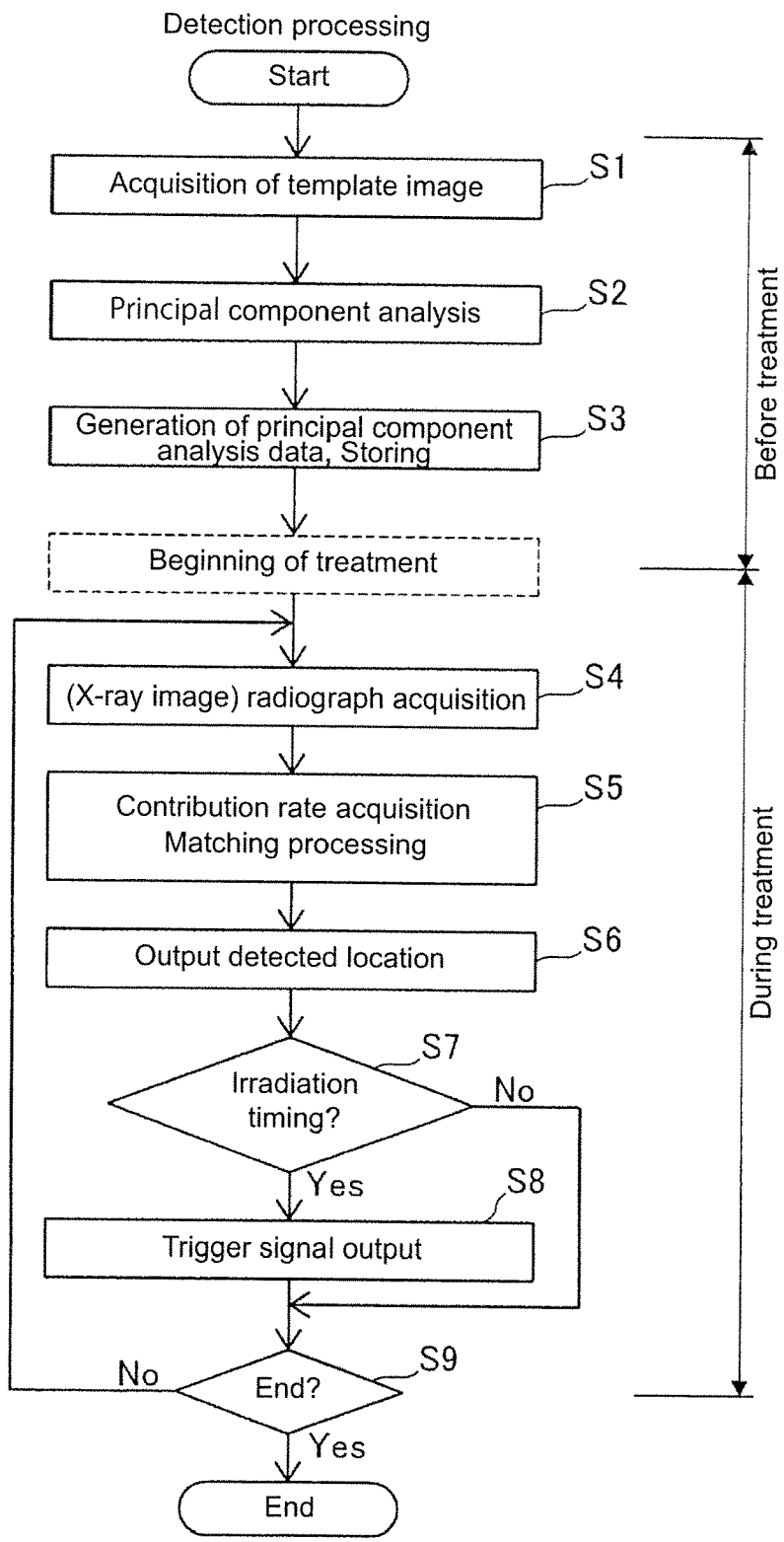
FIG. 7 is a flow chart illustrating a processing operation of the radiation imaging apparatus.

Next, referring to FIG. 7, the inventor sets forth the processing operation of the radiation imaging apparatus 100. Each step of processing is executed basically under the cooperation between the image processing element 5 (the image generation element 11 and the location detection elements 12) and the control element 4.

At the step S1, the image processing unit 5 acquires the template image 40. Specifically, as the preparation prior to the therapy, the X-ray image 30 is imaged in advance and the area including the specific region 50 is cut out (extracted) from the X-ray image 30 to provide the template image 40. The template image 40 can be made by the cut-put processing of the image processing unit 5 or the template image 40 that is made out at the separate situation can be read out from the network or the other memory medium.

At the step S2, the image processing unit 5 acquires the contribution rate cj of the principal component $V_j$ of the specific region 50 using the principal component analysis relative to a plurality of template images 40 incorporating the specific region 50 of the subject T. At the step S3, the image processing unit 5 makes out the principal component analysis data 23. Specifically, the location detection element 12 makes out the data from principal component $V_j$ by the above the Nth principal component, the projection matrix Q, each contribution rate $c_j$ and the average contribution rate vector $U_a$ of each template image 40 and stores, which are stored in the memory element 5b.

The following steps S4-S9 are processings during the particle beam treatment. At the step S4, the image processing unit 5 acquires the X-ray image 30. Specifically, the irradiation element 1 irradiates the radiation to the subject T, the X-ray detection element 2 detects the radiation that transmits through the subject T, and the image generation element 11 generates the X-ray image 30 based on the detection signal from the X-ray detection element 2. The X-ray image 30 is output to the location detection element 12 and the control element 4.

At the step S5, the image processing unit 5 executes the matching processing. Specifically, the location detection element 12 acquires the contribution rate (contribution rate vector W) relative to the image portion within the detection window 30a in the X-ray image 30. Then, the location detection element 12 executes the matching using the acquired respective contribution rates (the average contribution rate vector $U_a$ and the contribution rate vector W). As set forth above, the location detection element 12 shifts the detection window 30a and repeats the acquisition of the contribution rate (contribution rate vector W) at each location in the X-ray image 30 and the calculation of the square error $D^2$. And the location detection element 12 detects the location having the minimum square error $D^2$ as the specific region 50 within the X-ray image 30. In addition, two pairs of the irradiation element 1 and the X-ray detection element 2 are installed, so that the detection of the specific region 50 is executed respectively on the X-ray images 30.

At the step S6, the image processing unit 5 outputs the location of the specific region 50 detected from each X-ray image 30 to the control element 4. The control element 4 acquires the three-dimensional location of the specific region 50 based on the detected location of the specific region 50 in each X-ray image 30. The control element 4 superimposes the identification, which denotes the detected location of the specific region 50, to the acquired X-ray image 30 at the present time and displays such image on the display element 6 (updated display).

At the step S7, the control element 4 determines whether the timing is the irradiation timing for the therapeutic beam using the particle beam irradiation device 110 or not. Specifically, the control element 4 determines whether the three-dimensional location of the specific region 50 that is acquired this time is included within the irradiation location of the therapeutic beam along with the therapy plan in advance (irradiation range) or not.

In addition, whether the irradiation timing or not can be determined based on whether both locations of the two-dimensional specific region 50, which are detected in each X-ray image 30 in the two directions, are included in the irradiation location on the X-ray image 30 (irradiation range) or not. In such case, the control element 4 is not required to acquire the three-dimensional location of the specific region 50 based on the detected location of the specific region 50 in each X-ray image 30 at the step S6.

When the specific region 50 is included in the irradiation location, the control element 4 outputs the trigger signal to the particle beam irradiation device 110 at the step S8. When the specific region 50 is shifted from the irradiation location, the control element 4 proceeds the step S9 without outputting the trigger signal.

At the step S9, the control element 4 determines whether the particle beam therapy ends or not. When the particle beam therapy is kept ongoing, each processing of the steps S4-S8 is repeatedly executed. When the particle beam therapy ends this time, the detection processing and the control relative to the particle beam therapy end.

(Effect According to the Aspect of the Embodiment 1)

The following effects can be obtained according to the aspect of the Embodiment 1.

According to the aspect of the Embodiment 1, as set forth above, the location detection element 12 acquires each contribution rate ($c_j$, $c_{wj}$) of the principal component $V_j$ stored in the memory element 5b relative to each X-ray image 30 generated by the template image 40 and the image generation element 11 and detects the location of the specific region 50 from the X-ray images 30 based on a matching using each obtained contribution rate ($c_j$, $c_{wj}$). Thereby, the detection of the specific region 50 can be executed using the contribution rate ($c_j$, $c_{wj}$) to each template image 40 and each X-ray image 30 of the principal component $V_j$ acquired from the template image 40. In such case, the principal component analysis is not performed on the X-ray image 30 that is newly generated by the image generation element 11 and instead, the contribution rate $c_{wj}$ relative to the X-ray image 30 is just acquired using the result (principal component $V_j$) of the principal component analysis relative to the template image 40 prepared in advance (i.e., just needed to acquire the size of the projection vector), so that the detection processing can be achieved quickly. Then, the X-ray image 30 (the image including the noise) generated by the image generation element 11 is not used as-is and instead, the principal component $V_j$ of the template image 40 is used as a measure of the contribution rate $c_j$, so that the matching can be performed while suppressing the effect of the noise included in the X-ray image 30. As a result, even when the noise is included in the X-ray image 30, the specific region 50 can be detected quickly while the effect of the noise is being suppressed.

In addition, according to the aspect of the Embodiment 1, as set forth above, the location detection element 12 detects the location of the specific region 50 based on the difference (square error $D^2$) between the average value (average contribution rate vector $U_a$) of the contribution rates cj of the principal components $V_j$ relative to a plurality of template images 40 and the contribution rate $c_{wj}$ (contribution rate vector W) of the principal component $V_j$ relative to the X-ray images 30. Accordingly, the difference level of the X-ray image 30 from the common element (averaged image) to each template image 40, when the principal component $V_j$ is as a measure thereof, is obtained from the difference (square error $D^2$) of the contribution rates ($c_j$, $c_{wj}$) between (an average image of) each template image 40 and the X-ray image 30, so that the specific region 50 can be detected accurately based on that the difference level is getting smaller. In addition, the specific region 50 is detected by just performing the matching (calculation of the square error $D^2$) between contribution rates ($c_j$, $c_{wj}$) and it is different from the case in which the template matching is performed between the images, so that the high-speed detection can be achieved while suppressing the calculation amount.

For example, when compare the matching between the template image 40 having the (m×n) pixel and the X-ray image 30 and the matching between the contribution rates of the N-dimensional average contribution rate vector Ua using by the Nth principal component and the contribution rate vector W, the matching between images executes to calculate the (m×n) times square error D2 every pixel and in contrast, the matching between the contribution rates can be executed by calculating the square error $D^2$ only at most N times. Accordingly, the calculation amount can be largely cut.

In addition, according to the aspect of the Embodiment 1, the location detection element 12 performs the matching using from the first principal component $V_1$ to the Nth principal component $V_N$ (N is an integer between 2 and 100) that are stored in the memory element 5b. Accordingly, just the number N principal components up to 100 principal components are used, so that the detection of the specific region 50 can be executed quickly. In addition, the data needed to accurately detect the specific region 50 while removing the noise component can be included in the principal components up to the superordinate Nth, so that the detection processing can be performed with satisfactorily and required accuracy.

In addition, according to the aspect of the Embodiment 1, as set forth above, the location detection element 12 acquires the contribution rate cj using the principal component $V_j$ acquired from the template image 40 incorporating no secondary particle beam that occurs along with the particle beam treatment, detects the specific region 50 from each X-ray image 30 generated in series by the image generation element 11 during the particle beam treatment, and tracks the shift of the specific region 50.

The principal component $V_j$ acquired from the template image 40 having no incorporated secondary particle beam is applied, so that the effect of the secondary particle beam can be effectively canceled from the X-ray image 30 incorporating the secondary particle beam (noise). As a result, the effect of the secondary particle beam (noise) relative to the specific region 50 can be effectively suppressed.

In addition, according to the aspect of the Embodiment 1, as set forth above, the location detection element 12 acquires the contribution rate $c_{wj}$ relative to the image portion in the detection window 30a that is set up in the X-ray image 30 generated by the image generation element 11 and performs the matching using the contribution rate cwj by shifting the detection window 30a in series, by which the specific region 50 is detected from the X-ray image 30. Accordingly, in the case of the particle beam treatment, the area where the specific region 50 is present in the X-ray image 30 is understandable in accordance with the treatment plan data 22, so that the search area using the detection window 30a can be narrowed. As a result, the matching processing is no longer mandatory relative to the entire X-ray image 30, so that the detection processing can be further performed quickly.

[Embodiment 2]

Figure 8:
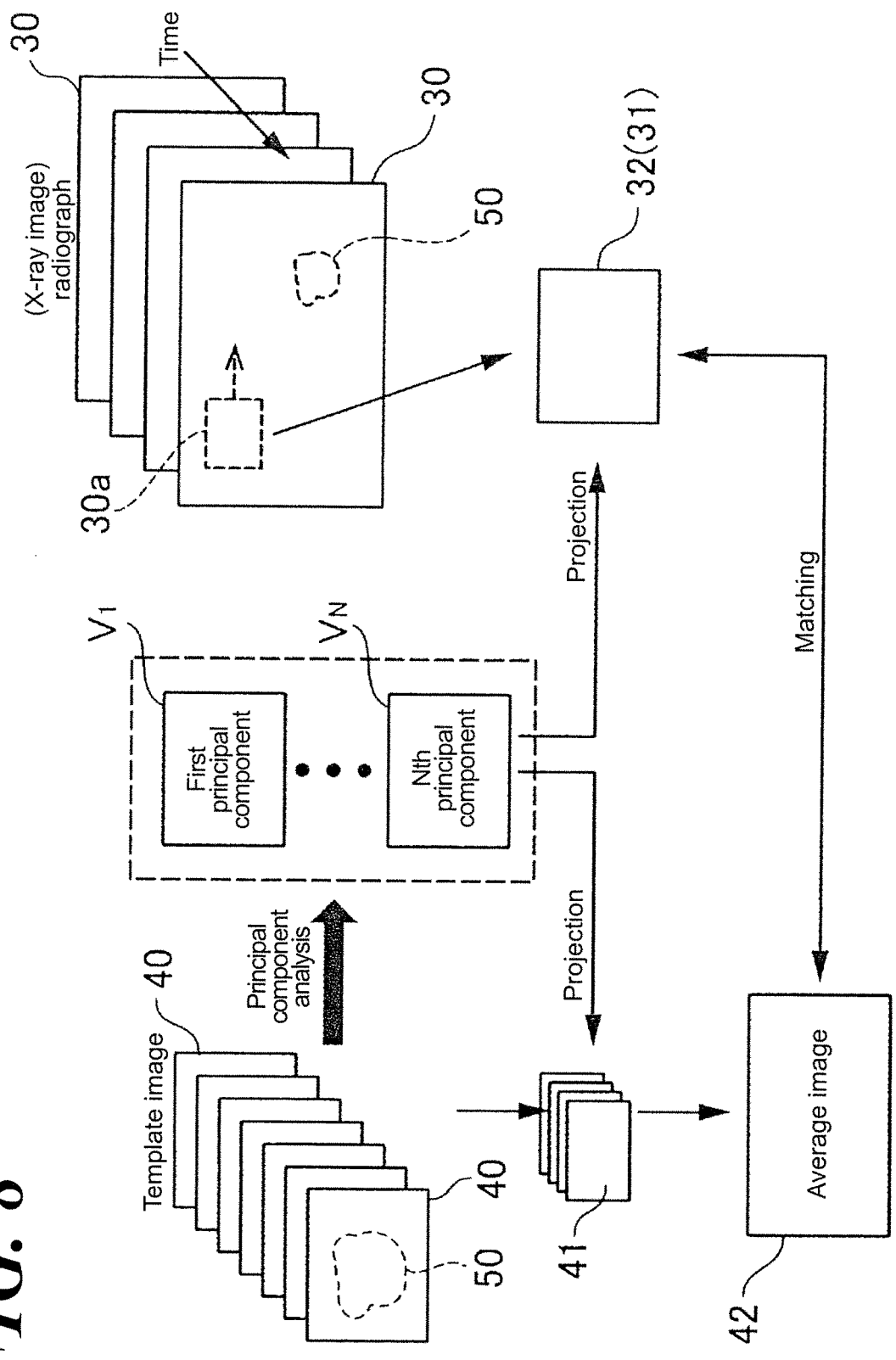
FIG. 8 is a schematic view illustrating a matching processing with the location detection element of the radiation imaging apparatus according to the aspect of the Embodiment 2.

Next, referring to FIG. 8, the inventor sets forth the radiation imaging apparatus according to the aspect of the Embodiment 2. According to the aspect of the Embodiment 2, the inventor sets forth the embodiment wherein the image is reconstructed using the principal component and the contribution rate to execute the matching between the images differently from the above Embodiment 1 wherein the matching relative to the contribution rate of the principal component relative to the template image 40 and the X-ray image 30 is executed. In addition, according to the aspect of the Embodiment 2, the contents of the matching processing by the location detection element are only different from the above aspect of the Embodiment 1, so that the explanation other than the matching processing is not provided here.

Referring to FIG. 8, the location detection element 12a (referring to FIG. 1) detects the location of the specific region 50 by matching the principal component image 41 of the template image 40 generated from the contribution rate cj relative to the template image 40 and the principal component $V_j$ and the conversion image 31 that is converted from the X-ray image 30 using the contribution rate cj and the principal component $V_j$ relative to the X-ray image 30. Specifically, according to the aspect of the Embodiment 2, the location detection element 12a reconstructs the image using each projection vectors ($c_jV_j$) indicated in the mathematical formula (2) by multiplying each principal component $V_j$ by the contribution rate ($c_j$, $c_{wj}$) relative to the respective template image 40 and the X-ray image 30.

Firstly, the location detection element 12a acquires the N-dimensional contribution rate vector $U_k$ obtained by multiplying each template image 40 by the projection matrix Q and generates the principal component image 41 (projection vector) of each template image 40 by multiplying each principal component $V_j$ by the contribution rate $c_{kj}$. According to the aspect of the Embodiment 2, the location detection element 12a generates the average image 42 of the principal component images 41 by averaging each generated principal component images 41. Specifically, the location detection element 12a averages the principal component images 41 on which the feature extraction is executed on each template image 40 using the components from the first principal component to the Nth principal component and calculates the average image 42 (average image vector H) considering from the first principal component to the Nth principal component and stores the results in the memory element 5b.

When detecting the specific region 50, the location detection element 12a acquires the contribution rate vector W by multiplying the generated X-ray image 30 by the image generation element 11 by the projection matrix Q and makes out the conversion image 31 relative to the principal component by multiplying each principal component $V_j$ by the contribution rate $C_{wj}$. Specifically, the conversion image 31 is the projection image 32 (projection image vector I), wherein the X-ray image 30 is projected by the components from the first principal component to the Nth principal component.

The location detection element 12a detects the location of the specific region 50 based on the difference between the average image 42 of a plurality (number k) of the principal component images 41 and the projection image 32 of the X-ray image 30. For example, the location detection element 12a obtains the square error $D^2$ between the average image 42 and the projection image 32 using the following mathematical formula (5).

[Mathematical formula 5]

$$D^2 = \|\vec{H} - \vec{I}\|^2 \tag{5}$$

Here, H is the vector of the average image 42 and I is the vector of the projection image 32.

In such way, the location detection element 12a detects the specific region 50 from the X-ray image 30. According to the aspect of the Embodiment 2, the principal component analysis data 23 includes each principal component $V_j$ acquired by the principal component analysis, the projection matrix Q, each contribution rate $c_j$, the principal component image 41 and the average image 42.

According to the aspect of the Embodiment 2, at the step S5 referring to FIG. 7, the location detection element 12a acquires the contribution rate (contribution rate vector W) relative to the image portion within the detection window 30a in the X-ray image 30 and reconstructs the projection image 32 from the contribution rate $c_{wj}$ and the principal component $V_j$. Then, the location detection element 12a executes the matching between the average image 42 and the projection image 32. As set forth above, the location detection element 12a shifts the detection window 30a and detects the location of the specific region 50 from the X-ray image 30 by repeating the generation of the projection image 32 relative to each location in the X-ray image 30 and the calculation of the square error $D^2$.

In other structural elements according to the aspect of the Embodiment 2 is the same as the aspect of the Embodiment 1.

(Effect According to the Aspect of the Embodiment 2)

According to the aspect of the Embodiment 2 as well as the Embodiment 1 as set forth above, the location detection element 12a acquires each contribution rate ($c_j$, $c_{wj}$) of the principal component Vj respectively relative to the template image 40 and the X-ray image 30 and detects the location of the specific region 50 from the X-ray images 30 based on the matching using each obtained contribution rate ($c_j$, $c_{wj}$). Even when the noise is included in the X-ray image 30, the specific region 50 can be detected quickly while the effect of the noise is being suppressed by using the contribution rate cj for which the principal component $V_j$ of the template image 40 is the measure (score).

In addition, according to the aspect of the Embodiment 2 as set forth above, the location detection element 12a detects the location of the specific region 50 by matching the principal component image 41 of the template image 40 generated from the contribution rate ckj relative to the template image 40 and the principal component $V_j$ and the conversion image 31 (projection image 32) that is converted from the X-ray image 30 using the contribution rate $c_{wj}$ relative to the X-ray image 30 and the principal component $V_j$. Therefore, the principal component image 41 (average image 42) and the conversion image 31 (projection image 32) are reconstructed using the acquired contribution rate ($c_{kj}$, $c_{wj}$) and the principal component $V_j$, so that the matching between images can be performed. Even in such case, the principal component image 41 (average image 42) that is converted by the principal component $V_j$ of the template image 40 and the conversion image 31 (projection image 32) are used, so that the matching can be performed while the effect of the noise included in the original X-ray image 30 is being suppressed.

[Alternative Embodiment]

In addition, the aspects of the Embodiments disclosed at this time are examples and not limited thereto in any points. The scope of the present invention is specified in the claims but not in the above description of the aspect of the Embodiments and all alternative (alternative examples) are included in the scope of the claims and equivalents thereof.

For example, according to the aspect of the Embodiments 1, 2 as set forth above, the location detection element 12 (12a) detects the specific region every frame relative to the X-ray image 30 in the video format, but the present invention is not limited thereto. According to the aspect of the present invention, when the frame rate of the video image is high, the specific region can be detected one time per a plurality of frames, but not frame-by-frame. In addition, the still image other than the video can be subject to the detection processing. In addition, the present invention can achieve to detect the specific region quickly using the contribution rate ($c_j$, $c_{wj}$) of the principal component $V_j$ without applying the principal component analysis relative to the radiation image that is being imaged, so that the present invention can be suitably applied to the radiation imaging apparatus for the use of taking care of the video, the use in the treatment in which the real-time detection processing is required and so forth, wherein a rapid detection processing is needed.

Further, according to the aspect of the Embodiments 1, 2 set forth above, one example, in which the radiation imaging apparatus is an X-ray imaging apparatus that takes an X-ray image using X-ray, but the present invention is not limited thereto. The present invention can be applied to the apparatus that performs an imaging using a radiation other than X-ray.

Further, according to the aspect of the Embodiments 1, 2 set forth above, the example is the radiation imaging apparatus that tracks the specific region 50 relative to the particle beam treatment, but the present invention is not limited thereto. The radiation imaging apparatus of the present invention can be applied to the use other than tracking the specific region 50 relative to the particle beam treatment. The present invention can be applied to any radiation imaging apparatus as long as such apparatus detects the specific region from the radiation image including a noise. The present invention can be applied suitably to a radiation imaging apparatus, wherein such apparatus detects the specific region from the radiation image including the noise, such as a secondary particle beam, that is hardly removed just only by using a general filtering processing.

Further, according to the aspect of the Embodiments 1, 2 set forth above, the example of the specific region 50 of the subject T is a tumor, but the present invention is not limited thereto. For example, when a marker is used to track the location of the tumor, the marker can be detected as the specific region 50 of the subject T.

In addition, according to the aspect of the Embodiment 1, the N-dimensional contribution rate vector Uk, in which the contribution rates $c_j$ of each principal component $V_j$ relative to the template image 40 with respect to the respective plurality (number k) of template images 40 are side by side, is made out and the average contribution rate vector $U_a$ is made out by averaging the contribution rate vectors $U_k$ of each template image 40, but the present invention is not limited thereto. According to the aspect of the present invention, for example, the N-dimensional contribution rate vector, in which the contribution rates $c_j$ of each principal component $V_j$ relative to the average image 42 of each template image 40 are side-by-side, is made out and the matching between such contribution rate vector relative to the average image 42 of each template image 40 and the contribution rate vector W (calculation of the square error $D^2$) can be executed.

In addition, according to the aspect of the Embodiments 1, 2 set forth above. for convenience of explanation, the inventors set forth a flow of the flow driving processing in which the processing of the image processing unit is executed following the processing flow, but the present invention is not limited thereto. According to the present invention, the processing of the image processing unit can be performed using an event driving processing (event driven processing) every event. In such case, a perfect event driven processing can be applied, or a combination of the event driven processing and flow driven processing can be applied.

REFERENCE OF SIGNS

1 Irradiation element
2 X-ray detection element (radiation detection element)
5*b* Memory element
11 Image generation element
12, 12*a* Location detection element
30 X-ray image (radiation image)
31 Conversion image
40 Template image
41 Principal component image
50 Specific region
100 Radiation imaging apparatus
c($c_j$, $c_{kj}$, $c_{aj}$, $c_{wj}$) Contribution rate
V($V_j$) Principal component As used herein, a "computer" or the apparatus for computer processing for an image or image processing unit etc. will be understood by those of skill in the art to comprises all of the elements required to function as discussed herein, such as, but not limited to, an input device for receiving data (detectors, image generation readers, etc.), an output device for outputting data in tangible form (e.g. data stream, data transfer, image file transfer, printing or displaying on a computer screen), one or more memories for storing data as well as operating computer code, and one or more processors (of any type suitable) for executing computer code wherein said computer code resident in said memory will physically cause said processor to read-in data via said input device, process said data within said processor and output said processed data via said output device.

It will be further understood by those of skill in the art that the apparatus and devices and the elements herein, without limitation, and including the sub components such as operational structures, circuits of all kinds, communication pathways, and related elements, control elements of all kinds, display circuits and display systems and elements, any necessary driving elements, inputs, sensors, detectors, memory elements, processors and any combinations of these structures etc. as will be understood by those of skill in the art as also being identified as or capable of operating the systems and devices and subcomponents noted herein and structures that accomplish the functions without restrictive language or label requirements since those of skill in the art are well versed in related radiation imaging apparatus and radiation image detection methods and diagnostic devices, computer and operational controls and technologies of radiographic devices and all their sub components, including various circuits and combinations of circuits without departing from the scope and spirit of the present invention.

Although only a few embodiments have been disclosed in detail above, other embodiments are possible and the inventors intend these to be encompassed within this specification. The specification describes certain technological solutions to solve the technical problems that are described expressly and inherently in this application. This disclosure describes embodiments, and the claims are intended to cover any modification or alternative or generalization of these embodiments which might be predictable to a person having ordinary skill in the art.

Those of skill would further appreciate that the various illustrative logical blocks, modules, circuits, and algorithm steps described in connection with the embodiments disclosed herein may be implemented as electronic hardware, computer software running on a specific purpose machine that is programmed to carry out the operations described in this application, or combinations of both. To clearly illustrate this interchangeability of hardware and software, various illustrative components, blocks, modules, circuits, and steps have been described above generally in terms of their functionality. Whether such functionality is implemented as hardware or software causing action to occur on the hardware depends upon the particular application and design constraints imposed on the overall system by the present invention. Skilled artisans may implement the described functionality in varying ways for each particular application, but such implementation decisions should not be interpreted as causing a departure from the scope of the exemplary embodiments.

The various illustrative logical blocks, modules, elements, and circuits described in connection with the embodiments disclosed herein, may be implemented or performed with a general or specific purpose processor, or with hardware that carries out these functions, e.g., a Digital Signal Processor (DSP), an Application Specific Integrated Circuit (ASIC), a Field Programmable Gate Array (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. The processor can be part of a computer system that also has an internal bus connecting to cards or other hardware, running based on a system BIOS or equivalent that contains startup and boot software, system memory which provides temporary storage for an operating system, drivers for the hardware and for application programs, disk interface which provides an interface between internal storage device(s) and the other hardware, an external peripheral controller which interfaces to external devices such as a backup storage device, and a network that connects to a hard wired network cable such as Ethernet or may be a wireless connection such as a RF link running under a wireless protocol such as 802.11. Likewise, an external bus may be any of but not limited to hard wired external busses such as IEEE-1394 or USB. The computer system can also have a user interface port that communicates with a user interface, and which receives commands entered by a user, and a video output that produces its output via any kind of video output format, e.g., VGA, DVI, HDMI, display port, or any other form. This may include laptop or desktop computers, and may also include portable computers, including cell phones, tablets such as the IPAD™ and Android™ platform tablet, and all other kinds of computers and computing platforms.

A processor or any kind (computer processing unit, microprocessor, inter-operative-circuits, etc.) may also be implemented as a combination of computing devices, e.g., a combination of a DSP and a microprocessor, a plurality of microprocessors, one or more microprocessors in conjunction with a DSP core, or any other such configuration. These devices may also be used to select values for devices as described herein.

The steps of a method or algorithm described in connection with the embodiments disclosed herein may be embodied directly in hardware, in a software module executed by a processor, using cloud computing, or in combinations. A software module may reside in Random Access Memory (RAM), flash memory, Read Only Memory (ROM), Electrically Programmable ROM (EPROM), Electrically Erasable Programmable ROM (EEPROM), registers, hard disk, a removable disk, a CD-ROM, or any other form of tangible storage medium that stores tangible, non-transitory computer based instructions. An exemplary storage medium is coupled to the processor such that the processor can read information from, and write information to, the storage medium. In the alternative, the storage medium may be integral to the processor. The processor and the storage medium may reside in reconfigurable logic of any type.

In one or more exemplary embodiments, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer.

The memory storage can also be rotating magnetic hard disk drives, optical disk drives, or flash memory based storage drives or other such solid state, magnetic, or optical storage devices. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer-readable media. The computer readable media can be an article comprising a machine-readable non-transitory tangible medium embodying information indicative of instructions that when performed by one or more machines result in computer implemented operations comprising the actions described throughout this specification.

Operations as described herein can be carried out on or over a web site. The website can be operated on a server computer, or operated locally, e.g., by being downloaded to the client computer, or operated via a server farm. The website can be accessed over a mobile phone or a PDA, or on any other client. The website can use HTML code in any form, e.g., MHTML, or XML, and via any form such as cascading style sheets ("CSS") or other.

The computers described herein may be any kind of computer, either general purpose, or some specific purpose computer such as a workstation. The programs may be written in C, or Java, Brew or any other programming language. The programs may be resident on a storage medium, e.g., magnetic or optical, e.g. the computer hard drive, a removable disk or media such as a memory stick or SD media, or other removable medium. The programs may also be run over a network, for example, with a server or other machine sending signals to the local machine, which allows the local machine to carry out the operations described herein.

Also, the inventors intend that only those claims which use the words "means for" are intended to be interpreted under 35 USC 112, sixth paragraph. Moreover, no limitations from the specification are intended to be read into any claims, unless those limitations are expressly included in the claims.

Having described at least one of the preferred embodiments of the present invention with reference to the accompanying drawings, it will be apparent to those skills that the invention is not limited to those precise embodiments, and that various modifications and variations can be made in the presently disclosed system without departing from the scope or spirit of the invention. Thus, it is intended that the present disclosure cover modifications and variations of this disclosure provided they come within the scope of the appended claims and their equivalents.

What is claimed is:

1. A radiation imaging apparatus, comprising:
   an irradiation element that irradiates a radiation to a subject;
   a radiation detection element that detects said radiation that transmits through said subject;
   an image generation element that generates a radiation image based on a detection signal from said radiation detection element;
   a memory element that stores a principal component of a specific region obtained by a principal component analysis relative to a plurality of template images incorporating said specific region of said subject; and
   a location detection element that acquires a contribution rate of said principal component that said memory element stores relative to each said template image and each said radiation image that said image generation element generates and detects a location of said specific region from said radiation image by a matching using each said obtained contribution rate.

2. The radiation imaging apparatus, according to claim 1, wherein:
   said location detection element detects the location of said specific region based on a difference between an average value of said contribution rates of said principal components relative to a plurality of said template images and said contribution rate of said principal component relative to said radiation image.

3. The radiation imaging apparatus, according to claim 1, wherein:
said location detection element executes said matching using components from a first principal component to a Nth principal component that said memory element stores, and a N is an integer between 2 and 100.

4. The radiation imaging apparatus, according to claim 1, wherein:
said location detection element acquires said contribution rate using said principal component acquired from said template image incorporating no secondary particle beam that occurs along with a particle beam treatment, detects said specific region from said respective radiation images generated in series by said image generation element during said particle beam treatment, and tracks a shift of said specific region.

5. The radiation imaging apparatus, according to claim 1, wherein:
said template image is an image that is extracted from said radiation image, which is acquired in advance, and includes said specific region, said location detection element acquires said contribution rate relative to an image portion in a detection window that is set up in said radiation image generated by said image generation element, executes said matching using said contribution rate by shifting said detection window in series, and detects said specific region from said radiation image.

6. The radiation imaging apparatus, according to claim 1, wherein:
said location detection element detects said location of said specific region by matching said principal component image of said template image generated from said contribution rate relative to said template image and said principal component and a conversion image that is converted from said radiation image using said contribution rate relative to said radiation image and said principal component.

7. A radiation image detection method, that detects a specific region from a radiation image of a subject, comprising steps of:
acquiring a principal component of said specific region by a principal component analysis;
relative to a plurality of template images incorporating said specific region of said subject;
generating said radiation image by irradiating a radiation to said subject and detecting said radiation that transmits through said subject;
acquiring a contribution rate of said principal component relative to each said template and each said radiation image; and
detecting the location of said specific region from said radiation image by the matching using each said obtained contribution rate.

* * * * *